United States Patent [19]

Yamazaki et al.

[11] Patent Number: 4,978,531

[45] Date of Patent: Dec. 18, 1990

[54] CLEBOPRIDE TRANSDERMAL PATCH

[75] Inventors: Keiko Yamazaki; Toshikuni Kawaji, both of Okawagun, Japan

[73] Assignee: Fordonal, S.A., Madrid, Spain

[21] Appl. No.: 231,034

[22] Filed: Aug. 11, 1988

[30] Foreign Application Priority Data

Aug. 13, 1987 [JP] Japan .................. 62-203311

[51] Int. Cl.[5] ............... A61F 13/02; A61L 15/06; A61K 9/70
[52] U.S. Cl. .................... 424/448; 424/449
[58] Field of Search .............. 424/448, 449, 447

[56] References Cited

U.S. PATENT DOCUMENTS

| | | | |
|---|---|---|---|
| 4,291,015 | 9/1981 | Kieth et al. .................. | 424/449 |
| 4,627,852 | 12/1986 | Vonbittera et al. . | |
| 4,664,857 | 5/1987 | Masao . | |
| 4,695,465 | 9/1985 | Kigasawa et al. . | |
| 4,820,715 | 4/1989 | Monkovic et al. .................. | 514/305 |

FOREIGN PATENT DOCUMENTS

| | | |
|---|---|---|
| 139127 | 5/1985 | European Pat. Off. . |
| 70986 | 8/1988 | European Pat. Off. . |
| 56-007434 | 2/1981 | Japan . |
| 58-215424 | 12/1983 | Japan . |
| 60-064923 | 4/1985 | Japan . |
| 61-021178 | 1/1986 | Japan . |

Primary Examiner—Thurman K. Page
Assistant Examiner—Leon R. Horne
Attorney, Agent, or Firm—Spencer & Frank

[57] ABSTRACT

A transdermal patch having a drug reservoir layer on a backing sheet, the drug reservoir layer comprises an adhesive gel base containing clebopride or a pharmaceutically acceptable salt thereof, the adhesive gel base containing as essential components, a water-soluble polymer, water and a water-holding agent. The use of such a patch permits adequate concentration of clebopride to be maintained in the blood over prolonged periods of time while avoiding the problems of multiple administrations of clebopride by conventional methods.

12 Claims, 2 Drawing Sheets

CLEBOPRIDE TRANSDERMAL PATCH

This relates to a clebopride-containing transdermal patch. More particularly the invention relates to a transdermal patch which allows stable long-term percutaneous absorption of the drug clebopride or a salt thereof.

Clebopride is a well known anti-emetic of the formula

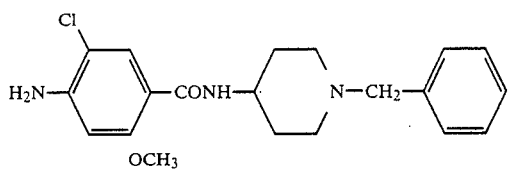

Clebopride acts on the trigger zone of chemoreceptors in humans to manifest anti-vomitting action, and is used as an anti-vomitting agent to inhibit nausea or vomitting after administration of antitumour drugs or levodopa preparations or after surgical operations. Clebopride has previously been administered orally, and normally supplied in the form of a salt, e.g., clebopride malate.

Although the known clebopride-containing antivomitting formulations exhibit excellent emesis-inhibiting effects, their oral administration causes the following drawbacks and presents problems in practical usage.

1. Oral administration during vomitting is difficult and the possibility of extracoporeal exclusion by vomitting is high even when it is initially accepted orally.

2. Absorption through the digestive organs is highly susceptible to the influences of pH in the gastro-intestinal tract and ingecta, etc., which cause individual differences in the absorption level of the drug. Therefore, when the drug is administered more or less in an excessive amount, side-effects are apt to appear on the mental and nervous systems to cause sleepiness, irritation, numbness, etc., and on the digestive system to cause constipation, thrist, diarrhoea, etc., or cause eruption, itching, or the like.

3. Due to the short biological half-life of clebopride of about 1.5 hours, once-a-day administration is insufficient to secure adequate activity, and furthermore, it is difficult to control its concentration in blood to the level below the side-effect manifesting level. Patients are consequently compelled to take the drug three times per day. With such frequent administration, it is difficult to effect complete prevention or therapy, as patients often forget to take the drug or are taken ill at bed time.

In order to overcome those problems with oral administration, we studied the possibility of administering clebopride topically in the form of ointments, gels or liquid preparations but the following problems were found:

(i) These topical preparations were applied by rubbing-in or spraying onto the skin. It is difficult to administer a predetermined dosage of clebopride in this manner, and the preparations are apt to soil hands, fingers and clothes of patients. While the soiling can be prevented by covering the site of application with gauze or the like, this is cumbersome.

(ii) Furthermore, because the solvents in these preparations evaporate, crystals of clebopride precipitate and percutaneous absorbability of clebopride is reduced. If the site of application is covered with a suitable film or the like to prevent the precipitation, it is likely to cause cutaneous allergic symptoms e.g. eruption, urticaria, etc., as the water content of stratum corneum of the skin becomes excessive.

Therefore, we continued our studies on still further methods of administration to discover that when a specific adhesive gel base composed essentially of a water-soluble polymer, water and a water-holding agent, is blended with clebopride or a salt thereof, the adhesive gel base exhibits a drug-release controlling function and, in spite of its water-holding property, good adhesive action to human skin, and at the same time, hydrates the stratum corneum of the skin. It was furthermore found that, because those actions work together to improve the quantitative percutaneous absorption of the drug, the above mentioned problems are substantially overcome, and still more, the minimal effective level of the drug concentration in blood can be maintained for several hours.

The present invention provides a clebopride-containing transdermal patch having a drug reservoir layer on a backing sheet, the drug reservoir layer comprising an adhesive gel base containing clebopride or a pharmaceutically acceptable salt thereof, the adhesive gel base containing, as essential components, a water-soluble polymer, water and a water-holding agent.

The water-soluble polymers that can be used in the invention include, for example, polyvinyl alcohol, gelatine, polyacrylic acid, solium polyacrylate, methylcellulose, carboxymethylcellulose, polyvinylpyrrolidone, gums and dextrines, or suitably cross-linked reaction products thereof having an improved cohesion. These polymers can be used either singly or in combination of two or more. These water-soluble polymers contribute to the desired physical properties, together with the other components of the adhesive gel base. The amount of the polymer component to be used varies to a certain extent depending on the specific polymer or polymers used, and types and physical properties of the other gel base components, but normally it may be selected within the range of 0.1 to 70% (all the percentages hereinafter appearing are by weight, unless otherwise specified), preferably 0.5 to 60%, to the total weight of the adhesive gel base. When it is less than 0.1%, the cohesion of the adhesive gel base is insufficient and shape retention is unsatisfactory, which may cause residues of the base to remain on the skin when the patch is peeled off. Furthermore, because the drug is released rapidly, drug in an amount higher than the permeation ratio on the outside of skin accumulates in the skin, which may induce skin irritation. On the other hand, if the concentration exceeds 70%, the base becomes hard in relation with the other components, which in turn leads to insufficient adhesiveness, deterioration in the affinity of the patch to the skin and reduced percutaneous absorption.

In the adhesive gel base used in the present invention, water is blended as a solvent for the drug or as a medium for drug migration (transfer). Hence, the release ratio of the drug to the skin is seriously affected by the evaporation of the water during the storage or use of the patch. It is therefore necessary to blend a water-holding agent in the gel base. When less than 1% of the water-holding agent is used, the intended water-holding effect cannot be obtained.

The water-holding agent used in the present invention can be, for example, glycols such as 1,3-butane diol, polyethylene glycol, or polyols such as glycerine, sorbitol, maltitol, etc. or saccharides. One or a mixture of more than one of those compounds can be used. The proportion of water-holding agent in the gel base is normally selected within the range of 1 to 70%, preferably 5 to 60%, of the adhesive gel base. Its use in an amount exceeding 70% is undesirable, as this invites reduction in gel strength in relation to the other components or incurs restriction on the amount of the drug to be blended. In order to further improve the water-retaining property, it is possible to blend a super hygroscopic polymer, such as starch-acrylonitrile graft polymer, starch-acrylic acid graft polymer, starch-styrenesulfonic acid graft polymer, starch-vinylsulfonic acid graft polymer, polyvinyl alcohol cross-linked product, acrylic acid-vinyl acetate saponified product, polyethylene glycol diacrylate cross-linked product, etc. Such a super hygroscopic polymer is preferably used in an amount not more than 10%, preferably within the range of 0.01 to 10%, based on the weight of the gel base.

The amount of water to be used in the patch of the present invention should be determined taking into consideration the solubility of the drug in water and the shape retention and adhesiveness of the adhesive gel base. Normally, it may be selected within the range of 10 to 90%, preferably 20 to 80%, of the weight of the adhesive gel base. When it is less than 10%, the amounts of the drug and the water-soluble polymer become subject to restriction, which renders the fomulation of a base of the concentration for optimum medicinal effect difficult, and also reduces the freedom of transfer of the drug in the base. In that case, a prolonged medicinal effect cannot be expected, and the good balance between the adhesiveness and shape retention of the adhesive gel base itself is impaired. On the other hand, when it exceeds 90%, blending of other components becomes difficult, and the adhesiveness and shape retention of the gel base cannot be maintained.

The adhesive gel base used in the patch of the present invention contains, as essential components, at least one water-soluble polymer, water and a water-holding agent as described above but it may optionally also contain, an absorption promotor (e.g. n-butyl stearate, benzyl alcohol, isopropyl myristate, isopropyl palmitate, polypropylene glycol, crotamiton, diethyl sebacate, etc.), a surfactant for emulsifying the absorption promotor in the water in the base, an antioxidant or an antiseptic for maintaining stability of the base, each in an appropriate concentration. When an antioxidant or an antiseptic is to be added, care should be taken about their influence on the drug release-controlling function or skin irritation.

It is preferred to adjust the pH of the adhesive gel base to a value between 4 to 7, to minimise skin irritation and optimise stability of the drug.

The adhesive gel base will contain clebopride or a pharmaceutically acceptable salt thereof. Experience with clebopride and its salts indicates the advantages of using the malate, citrate, hydrochloride, methane sulphonate or phosphate salts and such salts are preferably incorporated in the patch of the invention. The concentration of clebopride or its salt in the patch is not critical since inevitably some of the active substance will always remain on the patch and not be utilised clinically. The concentration will also be determined in part by the desired time period for which a particular patch is to be worn by the patient. These considerations point to an initial clebopride or salt concentration on the patch of 100–600 micrograms/cm$^2$, preferably about 300 micrograms/cm$^2$.

The clebopride-containing transdermal patch of the present invention can be manufactured by blending the above-described adhesive gel base with the desired amount of clebopride or salt thereof (e.g., clebopride malate) as the effective ingredient and coating the resulting gel base onto a suitable backing or support to form a drug reservoir layer on the backing. Furthermore, a liner of suitable material may be attached to the surface of the drug reservoir layer to protect it and prevent evaporation of water from it during storage.

The backing sheet is preferably a pliable material capable of following the movement of human body at least to some extent, for example, various types of non-woven fabric, woven fabric, spandex, flannel, or those materials laminated with polyethylene film, polyvinyl chloride film, ethylene-vinyl acetate film, polyurethane film, etc.

The transdermal patch of the present invention having the above-described structure permits the drug to be quantitatively released, its method of use is simple and long-term application is possible.

BRIEF DESCRIPTION OF THE DRAWINGS

The drawings show the results of pharmacological tests of the transdermal patch of the present invention as obtained in the Examples.

Figure 1:
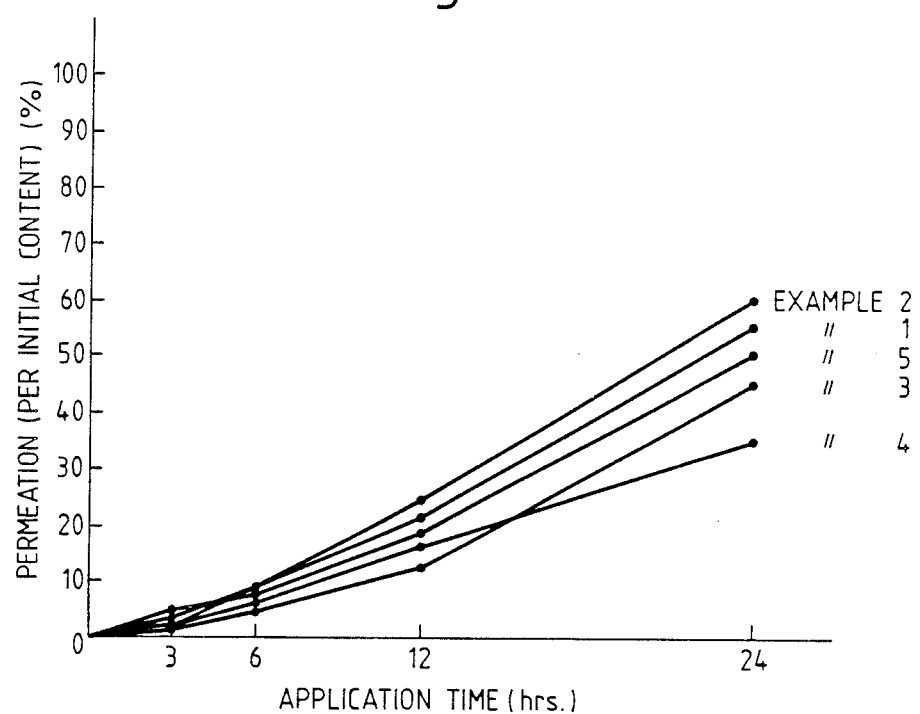
FIG. 1 is a graph showing the relation between drug permeation and application time of the patch.

The present invention will be more specifically explained with reference to the following Examples, with the understanding that the invention is not restricted to these specific arrangements.

EXAMPLE 1

| Components | w/w % |
|---|---|
| Polyvinyl alcohol (average degree of saponification: at least 95%) | 10.5 |
| Glycerine | 5.0 |
| Karaya gum | 1.5 |
| Clebopride malate | 1.5 |
| Purified water | 81.5 |

A drug-containing adhesive gel base was prepared using the above components, and a transdermal patch was then prepared. The above-mentioned components, other than clebopride malate, were stirred together and heated to about 40° C., and thereafter clebopride malate was introduced followed by further stirring. This drug containing adhesive gel base (pH=5.0) was then coated, in an amount of 200 g/m$^2$, to form a drug reservoir layer on a backing formed of rayon non-woven fabric laminate-processed with an ethylene-vinyl acetate film. A liner of silicon-processed polyethylene terephthalate film (PET film) was applied on the surface of the layer and the patch was cut to desired size to provide the transdermal patch for use by the patient. The drug content of the patch was 300 μg/cm$^2$.

EXAMPLE 2

The procedure of Example 1 was followed except that the following components were used to give a transdermal patch of drug content: 300 μg/cm² and pH 5.0 in the gel base.

| Components | w/w % |
|---|---|
| Polyvinyl alcohol (average degree of saponification: at least 95%) | 9.0 |
| Glycerine | 15.0 |
| Dextrin | 4.0 |
| Clebopride malate | 1.5 |
| Purified water | 70.5 |

EXAMPLE 3

The procedure of Example 1 was followed except that the following components were used to give a transdermal patch of drug content: 300 μg/cm² and pH 6.0 in the gel base.

| Components | w/w % |
|---|---|
| Polyvinyl alcohol (average degree of saponification: at least 95%) | 5.0 |
| Sodium polyacrylate | 3.0 |
| Carboxymethylcellulose | 3.0 |
| Polyacrylic acid | 2.0 |
| 70% Sorbitol | 30.0 |
| Clebopride malate | 1.5 |
| Purified water | 55.5 |

EXAMPLE 4

The procedure of Example 1 was followed except that the following components were used to give a transdermal patch of drug content: 300 μg/cm² and pH 7.0 in the gel base.

| Componenets | w/w % |
|---|---|
| Gelatine | 3.0 |
| Polyvinylpyrrolidone | 1.0 |
| Sodium polyacrylate | 3.0 |
| Carboxymethylcellulose | 3.0 |
| Starch-acrylic acid graft polymer [Sanwet IM-300, product of Sanyo Kasei Kogyo K. K.] | 0.10 |
| Glycerine | 30.0 |
| 70% Sorbitol | 15.0 |
| Clebopride malate | 1.5 |
| Propyl p-hydroxybenzoate | 0.05 |
| Purified water | 43.35 |

EXAMPLE 5

| Components | w/w % |
|---|---|
| Urethane prepolymer | 10.0 |
| Propylene glycol | 10.0 |
| 1,3-Butanediol | 8.0 |
| Glycerine | 20.0 |
| Clebopride malate | 1.5 |
| Purified water | 50.5 |

All of the above components, other than clebopride malate, were mixed together and the mixture together with the urethane prepolymer was coated on a backing sheet of the type used in Example 1 in an amount of 200 g/m², using a two-liquids type spray device for the urethane. After the coat gelled, a PET film liner was applied on the surface of the gel layer and the whole system was cut to provide the transdermal patch.

The transdermal patches obtained in the foregoing Examples were subjected to the following pharmacological tests.

TEST 1

Using a Frantz's diffusion cell, the amount of clebopride malate permeable through alvine skin of rats was determined by high pressure liquid chromatography.

A circle of 2 cm in diameter was stamped out from each of the sample patches (clebopride malate content: 942 g), and attached onto the rat skin in the diffusion cell. A pH 6.8 phosphoric acid buffer was used(n=6) on the receptor side. The results are shown in FIG. 1 which shows that, during 24 hours continuous application, the skin permeation of the drug continuously takes place, exhibiting a good permeation ratio.

TEST 2

Figure 2:
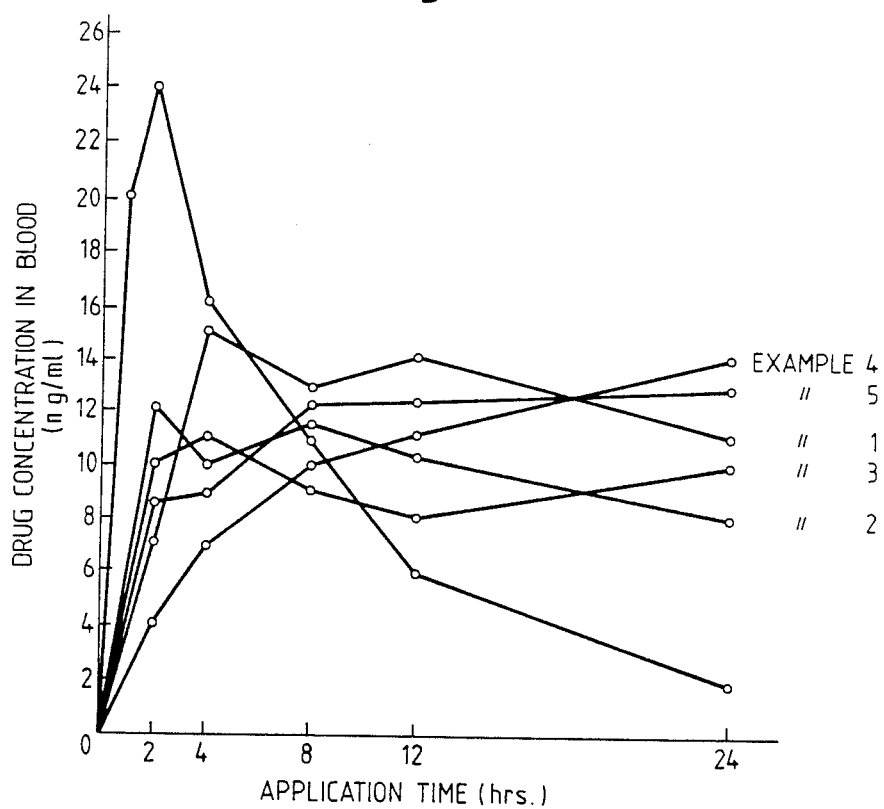
FIG. 2 is a graph showing the relation between drug concentration in blood and application time of the patch.

The abdominal region of beagle dogs was shaved and a 5 cm×5 cm size patch from each sample (clebopride malate content: 7.5 mg) was applied to the shaved region. Blood samples were then extracted from the dogs at fixed intervals at the rate of 5 ml per dog each time. The clebopride free base content in the serum was measured by a radioimmunoassay and the results are shown in FIG. 2. Simulaneously apomorphine (20 μg/kg) was administered to each dog by intravenous injection and the number of times of vomitting was recorded (n=3). The results are given in Table 1.

CONTROL

As controls, soft gelatine capsules containing 4 mg of clebopride malate were administered orally and a similar test was conducted.

TABLE 1

| Sample | Control A | B | Appln. time 2 hrs. A | B | Appln. time 4 hrs. A | B | Appln. time 8 hrs. A | B | Appln. time 12 hrs. A | B | Appln. time 24 hrs. A | B |
|---|---|---|---|---|---|---|---|---|---|---|---|---|
| Example 1 | 4, 3, 5 | — | 0, 0, 1 | 66.7 | 0, 0, 0 | 100 | 0, 0, 0 | 100 | 0, 0, 0 | 100 | 0, 0, 0 | 100 |
| 2 | 3, 4, 3 | — | 0, 0, 0 | 100 | 0, 0, 0 | 100 | 0, 0, 0 | 100 | 0, 0, 0 | 100 | 0, 0, 0 | 100 |
| 3 | 2, 3, 3 | — | 0, 0, 0 | 100 | 0, 0, 0 | 100 | 0, 0, 0 | 100 | 0, 0, 0 | 100 | 0, 0, 0 | 100 |
| 4 | 3, 3, 5 | — | 1, 0, 1 | 33.3 | 0, 0, 0 | 100 | 0, 0, 0 | 100 | 0, 0, 0 | 100 | | |
| 5 | 4, 6, 2 | — | 1, 2, 0 | 33.3 | 0, 0, 0 | 100 | 0, 0, 0 | 100 | 0, 0, 0 | 100 | 0, 0, 0 | 100 |

TABLE 1-continued

| Sample | Control A | B | Appln. time 2 hrs. A | B | Appln. time 4 hrs. A | B | Appln. time 8 hrs. A | B | Appln. time 12 hrs. A | B | Appln. time 24 hrs. A | B |
|---|---|---|---|---|---|---|---|---|---|---|---|---|
| Control 1 | 4, 5, 3 | — | 0, 0, 0 | 100 | 0, 0, 0 | 100 | 0, 0, 0 | 100 | 0, 0, 0 | 100 | 0, 1, 0 | 66.7 |

Note
In the table, in each column:
the three figures in each A column is the number of times of vomitting of each of the three test dogs.
the figure in each B column is the % inhibition.

EXAMPLE 6

The procedure of Example 1 was followed except that the following components were used to give a transdermal patch of drug content 525 μg/cm² and pH 7.0 in the gel base in which this example was coated on the backing in an amount of 350 g/m².

Patches measuring 3.5×3.5 cm and actually carrying 4.82 mg clebopride as free base or measuring 3.5×5.0 cm and actually carrying 6.88 mg clebopride free base were tested as described in Test 2 above. The patch was removed from the dog after 24 hours. Table 2 shows the frequency of vomiting after apomorphine injection. Table 3 shows in ng/ml the concentration of clebopride free base in the serum of the test dogs measured at the times indicated.

TABLE 2

| | Dose | | | | | | | | | | |
|---|---|---|---|---|---|---|---|---|---|---|---|
| | 3.5 × 3.5 cm patch | | | | 3.5 × 3.5 cm patch | | | | | | |
| | Dog | | | | | | | | | | |
| | A | B | E | G | A | B | C | D | E | F | G | H |
| | Weight (kg.) | | | | | | | | | | |
| | 11.5 | 11.0 | 10.0 | 10.0 | 11.5 | 11.0 | 10.0 | 10.0 | 10.0 | 12.0 | 10.0 | 9.5 |
| Hrs. after patch application | | | | | | | | | | | | |
| 0 | 4 | 3 | 2 | 4 | 4 | 3 | 2 | 3 | 2 | 3 | 4 | 3 |
| 12 | 3 | 0 | 0 | 0 | 0 | 0 | 0 | 0 | 0 | 0 | 0 | 0 |
| 24 | 0 | 0 | 0 | 0 | 0 | 0 | 0 | 0 | 0 | 0 | 0 | 0 |
| Hrs. after patch removal | | | | | | | | | | | | |
| 24 | 0 | 0 | 0 | 0 | 1 | 2 | 0 | 1 | 0 | 1 | 1 | 2 |
| 48 | 1 | 2 | 0 | 3 | 2 | 2 | 0 | 3 | 0 | 1 | 1 | 2 |

TABLE 3

| | Dose | | | | | | | | | | |
|---|---|---|---|---|---|---|---|---|---|---|---|
| | 3.5 × 3.5 cm patch | | | | 3.5 × 5.0 cm patch | | | | | | |
| | Dog | | | | | | | | | | |
| | A | B | E | G | A | B | C | D | E | F | G | H |
| | Weight (kg.) | | | | | | | | | | |
| | 11.5 | 11.0 | 10.0 | 10.0 | 11.5 | 11.0 | 10.0 | 10.0 | 10.0 | 12.0 | 10.0 | 8.5 |
| 0 (hr) | 0 | 0 | 0 | 0 | 0 | 0 | 0 | 0 | 0 | 0 | 0 | 0 |
| Hrs. after patch appln. | | | | | | | | | | | | |
| 6 | — | 8.80 | 6.72 | 4.34 | 0.80 | 1.80 | 5.05 | 3.27 | 5.84 | 6.88 | 2.48 | 1.16 |
| 12 | 0.07 | 8.48 | 9.30 | 3.86 | 7.89 | 2.36 | 4.31 | 4.41 | 5.71 | 4.82 | 1.93 | 1.60 |
| 24 | 5.88 | 5.38 | 9.22 | 4.26 | 4.17 | 3.51 | 5.85 | 4.33 | 4.60 | 5.46 | 2.89 | 3.19 |
| Hrs. after patch removal | | | | | | | | | | | | |
| 12 | 6.13 | 2.29 | 4.18 | 1.05 | 2.18 | 1.48 | 1.99 | 3.03 | 2.24 | 2.13 | 0.92 | 1.38 |
| 24 | 2.60 | 1.54 | 2.53 | 1.88 | 1.03 | 0.81 | 1.47 | 1.39 | 1.16 | 2.32 | 4.26 | 1.44 |
| 48 | 0.81 | 0.75 | 1.23 | 0.31 | 0.87 | 0.72 | 0.45 | 0.63 | 0.39 | 0.75 | 0.45 | 1.28 |

| Component | w/w % |
|---|---|
| PVA (average degree of saponification: at least 95%) | 15.0 |
| Propylene glycol | 1.0 |
| Dextrin | 0.5 |
| Clebopride malate | 1.5 |
| Purified Water | 82.0 |

We claim:

1. A transdermal patch having a drug reservoir layer on a backing sheet, the drug reservoir layer comprising an adhesive gel base containing clebopride or a pharmaceutically acceptable salt thereof, the adhesive gel base containing as essential components, a water-soluble polymer, water and a water-holding agent selected from the group consisting of glycerine, 1, 3-butane-diol, sorbitol maltitol, polyethylene glycol and a saccharide.

2. A patch according to claim 1 wherein the water soluble polymer is selected from the group consisting of polyvinyl alcohol, gelatine, polyacrylic acid, sodium polyacrylate, methylcellulose, carboxymethylcellulose, polyvinylpyrrolidone and a gum or dextrin or a cross-linked reaction product thereof.

3. The patch according to claim 1 containing 0.5–60% by weight water-soluble polymer based on the weight of the adhesive gel base.

4. The patch according to claim 1 wherein the water-holding agent is present in an amount of 5–60% by weight of the adhesive gel base.

5. The patch according to claim 1 wherein water is present in an amount of 20–80% by weight of the adhesive gel base.

6. The patch according to claim 1 where the pH of gel base is 4 to 7.

7. The patch according to claim 1 wherein the concentration of clebopride or salt thereof is 100 to 600 $\mu g/cm^2$.

8. The patch according to claim 1 wherein the adhesive gel layer is protected before use with a liner sheet.

9. The patch according to claim 1 wherein the backing sheet is a pliable non-woven fabric or is a pliable laminate.

10. The method of preparing a transdermal patch which comprises forming an adhesive gel base by blending clebopride or a pharmaceutically acceptable salt thereof with water, a water-holding agent selected from the group consisting of glycerine, 1, 3butane-diol, sorbitol, maltitol, polyethylene glycol and a saccharide and a water-soluble polymer and coating the resulting adhesive gel base onto a backing sheet.

11. The patch according to claim 1 wherein the water-holding agent is a glycol.

12. The patch according to claim 1 wherein the water-holding agent is a polyol.

* * * * *